United States Patent [19]

Wang et al.

[11] 4,105,025

[45] Aug. 8, 1978

[54] SURGICAL SUPPORT

[75] Inventors: Yen Wang, 6883 Reynolds St., Pittsburgh, Pa. 15208; Wen-Hsuan Chang, Gibsonia, Pa.

[73] Assignee: Yen Wang, Pittsburgh, Pa.

[21] Appl. No.: 741,295

[22] Filed: Nov. 12, 1976

[51] Int. Cl.$^2$ ............................................. A61F 13/04
[52] U.S. Cl. ................................... 128/90; 428/425
[58] Field of Search .................. 128/90, 150; 428/425

[56] References Cited

U.S. PATENT DOCUMENTS

| | | | |
|---|---|---|---|
| 2,650,212 | 8/1953 | Windemuth | 128/90 |
| 3,048,169 | 8/1962 | Pierce | 128/90 |
| 3,656,476 | 4/1972 | Swinney | 128/90 |

OTHER PUBLICATIONS

*Encyclopedia of Polymer Science and Technology*, vol. 11, Interscience Publishers, New York, 1969, pp. 506-513 and 526-527.

*Primary Examiner*—Benjamin R. Padgett
*Assistant Examiner*—Deborah L. Kyle
*Attorney, Agent, or Firm*—Stanley J. Price, Jr.; John M. Adams

[57] ABSTRACT

A supportive wrapping for a surgical support or orthopedic cast is produced by providing a bandage material which is impregnated or coated with a molten polyurethane polymer that is crystallizable in a predetermined, delayed time period at room temperatures or at temperatures tolerable to human skin and permitting the polyurethane polymer to crystallize on the bandage material to form a strong, supportive, self adhered wrapping while standing at or cooling to room temperature.

5 Claims, No Drawings

SURGICAL SUPPORT

BACKGROUND OF THE INVENTION

1. Field of the Invention

This invention relates to both means for and methods of preparing an improved supportive wrapping for surgical supports or the like and, more specifically, to a unique, immobilizing and/or protective body support or cast comprised of a bandage material impregnated or coated with a crystallized polyurethane polymer, preferably, formed directly on the bandage material and which is specially prepared to render desired handling and use properties previously unavailable when employing prior art surgical support or orthopedic cast techniques.

2. Description of the Prior Art

The traditional surgical support or body cast for immobiliztion and/or protection of an afflicted portion of the body during healing is a gauze and plaster of Paris composite. Some of the well known shortcomings of this traditional approach involve heaviness, bulkiness, water sensitivity, dust collection, lack of transparency to X-rays, difficulty of removal, lack of flexibility and discomfort of exothermic heat evolved during drying of the cast. These and other shortcomings have led to the proposal of surgical supports or body casts composed of other materials or combinations of materials. In particular, with the advance of polymer technology, much attention has been given to the effective utilization of plastics to overcome the deficiencies of the plaster of Paris cast.

One approach that has been taken in utilizing plastics technology is disclosed in U. S. Pat. No. 3,302,642. As therein disclosed, it is proposed to extrude a net-like polymer fabric, specifically, a vinylidene chloride polymer fabric, wind the fabric on a spool and supercool the entire spool with the wound material thereon before crystallization or substantial crystallization can occur. When supercooled to temperatures down to $-100°$ C, the polymer fabric can be maintained without significant crystallization for a period of 2 weeks or more. For application or use, the polymeric fabric is allowed to warm to room temperature until pliable. Then it is cut to the desired shape and applied to the patient by wrapping. The loose ends are weakly held together with clips or stitches or other fastening means. Within 10 to 20 minutes at room temperature, the polymeric fabric will crystallize and stiffen sufficiently to provide a surgical or body support.

Another approach, claiming similar utility to the foregoing, is disclosed in U.S. Pat. No. 3,728,206. In accordance with this latter disclosure, it is proposed to provide a composite, supportive non-thermoplastic foam web impregnated with a matrix of foam-like thermoplastic material which, upon heating, can be readily molded to an injured limb and, thereafter, allowed to cool, crystallize and harden to form an orthopedic bandage or wrap. However, since this approach, like the prior approach, is based upon providing a premanufactured product of limited shelf life because of the nature of the thermoplastic matrix materials disclosed, special packaging arrangements, the addition of chemical stabilizers and special handling conditions are proposed or found essential to preserve the useful life of the product for any appreciable period of time. Notwithstanding, as distinguished from the prior disclosure wherein clips, stitches or the like are required for weakly holding loose ends of the bandage together, the thermoplastic matrix of the bandage of this latter disclosure is generally cohesive at the elevated temperatures of application to the patient and, accordingly, provides a self-adhesive bandage.

Some other approaches that have been taken in utilizing plastics technology are disclosed in U.S. Pat. Nos. 2,301,426, 2,375,365, 2,483,715, 2,582,242, 2,616,418, 2,759,475, 2,800,129, 3,420,231, 2,467,086, 3,490,444, 3,501,427, 3,592,190, 3,656,476, 3,674,021, 3,692,023, 3,763,858;and British Pat. No. 1,155,556, the disclosures of which, like those of the aforementioned patents, are incorporated herein by reference.

Generally, the development of the state of the art of plastic supports has heretofore found limited acceptance because of the presence of one or more deficiencies, including: use of solvents that are potentially toxic, air polluting, deleterious to the skin or inflammable; deficiencies in desired physical and/or chemical properties; lack of rigidity, insufficient rigidity or insufficient flexibility in the support; difficulties in handling, preparation, use and limited shelf life; the presence of exothermic heat during curing or polymerization; inflexibility in use or application due to the properties of materials being inexorably fixed during premanufacture and, also, attendant limitations on the shape or form of materials made available as premanufactured products. Accordingly, there is a need for improvements in the application of polymer technology to the field of orthopedic supports and body casts.

SUMMARY OF THE INVENTION

In accordance with the present invention, there is provided a supportive wrapping for a surgical support or body cast comprised of a suitable substrate, such as a preforated fabric, a net like structure or the like, impregnated or coated with a crystallized polyurethane polymer material. The crystallized polyurethane polymer material is preferably comprised of either a polyester or polyether polyol, more preferably a diol, and a polyisocyanate, preferably a diisocyanate. Generally the desired supportive wrapping for the orthopedic support or body cast of this invention is produced by providing a bandage material which is impregnated or coated with a molten polyurethane polymer that is crystallizable in a predetermined delayed time period at room temperatures or at temperatures tolerable to human skin and permitting the polyurethane polymer to crystallize on the bandage material to form the desired strong, supportive, self adhered wrapping while standing at or cooling to room temperature.

By following the teachings of this invention, there is provided a supportive wrapping for a surgical support or body cast employing materials that are readily available and easily prepared or modified in situations to suit the specific procedural or medical exigencies dictated by a particular injury or type of injury. The polymer component or polymer forming materials of the surgical support or bandage are castable, as well as susceptible of other techniques of application. It is additionally self-adhesive, usable at a temperatures tolerable to human skin and room temperature setting. The bandage material that it produces is characterized by virtually unlimited shelf life, it is reusable, i.e., it can be removed for reexamination of a wound and then used to redress the wound and can be packaged in a conventional manner, such as the use of a polyethylene bag. Also, it may be conveniently provided in roll form from which it is freely removed and applied. Furthermore, no specialized equipment other than the normal availability of moderate heat, such as supplied by a regular oven, hot water or hot air, is required. Moreover, the support produced by this invention possesses optimum physical and chemical properties and is light weight, ozone resistant, washable, X-ray transparent, durable and non-brittle and easy to prepare, apply and remove.

DESCRIPTION OF PREFERRED EMBODIMENTS

This invention encompasses the use of a crystallizable polyurethane comprised of a selected polyol and a selected polyisocyanate combined together in certain proportions and heated in a molten state to produce a self-adhesive polyurethane polymer having a melting point of about 100°–160° F (37.8°–71° C) and possessing other desirable physical and/or chemical properties. More specifically, the polyurethane is used as an improved adhesive, coating, casting or impregnating material when applied to a bandage in the process of making a surgical support, body cast or similar medical appliance. In particular, this invention contemplates using a polyol that is normally crystalline and has a high molecular weight, i.e., a molecular weight greater than 750. Moreover, the polyol employed must have a melting point below 250° F (121.1° C), preferably below 212° F (100° C) and more preferably, a melting point in the range of 100°–212° F (37.8°–100° C).

The criteria for the polyisocyanate used are less critical except that it must be present with the polyol in such a minor amount, generally between about 5 to 45 percent and preferably, between about 5 to 20 percent by weight based on the total weight of the two constituents, such that a substantially completely crystallizable polyurethane polymer is produced. In addition, the amount of polyisocyanate used is such that it will delay the time of crystallization for a period of 2 to 40 minutes, preferably 10 to 20 minutes at a temperature of 20° F ($-6.6°$ C) to 150° F (65.5° C) preferably between 60° F (15.6° C) and 100° F (37.9°C), i.e., temperatures that are easily tolerated by both the doctor and the patient.

The polyols that are contemplated for use with this invention include the crystalline polyester diols and the crystalline polyether diols with a melting point of 100°–250° F (37.8°–121.1° C. Suitable polyester diols that may be used are disclosed in the book entitled "Polyesters", by Vasilii Vladimrovich Korshak, translated from Russian by B. J. Hazzard, edited by J. Burdon and published by Pergamon Press, Oxford, New York 1965, the disclosure of which is incorporated herein by reference. Desirable polyether diols that are usable include polyethylene ether glycol, polytetramethylene ether glycol and other ether glycols of a melting point less than 250° F (121.1° C). Particularly preferred are polytetramethylene glycol adipate and polyhexamethylene glycol adipate with a molecular weight of 1000–2500, because of their ready availability and because they give the desired combined properties sought in connection with this invention.

The polyisocyanate used is preferably a diisocyanate selected from those disclosed in the book entitled "Diisocyanates" by A. A. R. Sayigh, Henri Ulrich and William J. Farrissey, Jr., available from the Upjohn Company, North Haven, Conn. and reprinted from a chapter in the book "Condensation Monomers" by the same authors and published by John Wiley & Sons, Inc., the disclosures of which are incorporated herein by reference. The preferred diisocyanates are toluene diisocyanate (TDI) and methylene bis (4-phenyl isocyanate) MDI) because of their ready availability. The above materials tend to become yellow upon exposure. When non-yellowish material is desirable, hydrogenated TDI or MDI may be used for TDI or MDI.

Other materials, such as monools, triols, monoisocyanates and triisocyanates, in minor amounts may be used. Again the criteria are the melting point and the rate of crystallization of the product. Some acid groups may also be included. Also, catalysts may be used to facilitate the reaction. Should a basic background on crystalline polyurethanes be necessary or desirable for a fuller understanding of this invention, reference is made to the series of monographs, entitled "High Polymers", and, in particular, to Volume XVI, Part I, entitled "Polyurethanes — Chemistry and Technology", by J.H. Saunders and K.C. Frisch, published by Interscience Publishers, New York, N.Y. 1962, the disclosure of which is incorporated herein by reference.

The fabric, carrier base or bandage material employed with the crystallizable polyurethane polymer may be of any suitable natural or synthetic composition and may be knitted, woven or nonwoven as desired. Preferably, it is a foraminous or porous material possessing some degree of absorptivity, such as surgical gauze, and, most preferably, a material that is stretchable in one or two dimensions.

To illustrate a specific embodiment of this invention, reference is made to the following:

EXAMPLE 1

In a suitable vessel, molten hydroxyl-terminated butanediol adipate having a molecular weight of about 2000 is combined with methylene bis (4-phenyl isocyanate) in a 1:1 molar ratio. The molten mixture is applied to an "ACE" brand bandage, supplied by Becton, Dickinson and Company of Rutherford, N.J., and the impregnated or coated bandage is placed in an oven maintained at a temperature at which polymerization will proceed to completion, such as about 212° F (100° C). The bandage material is then formed into a roll while the polymer is still in a molten state. The polymer on the so-formed roll will crystallize on standing at room temperature. Either before or after the crystallization occurs, this roll may be packaged and thereafter, sold or stored for subsequent use.

As an alternative to the above procedure, it is also possible to form the impregnated or coated bandage material into a roll before polymerization. This roll is then heated in an oven or the like until polymerization proceeds to completion or substantial completion. The so-formed roll will crystallize on standing at room temperature, either before or after which, as aforesaid, it may be packaged and, thereafter, sold or stored for use.

As a further alternative to either of the above procedures, it is additionally possible to polymerize the impregnated or coated bandage material in a heated oven or the like and then permit the polymer to crystallize or substantially crystallize before forming the bandage material into a roll. As before, after forming the bandage material into a roll, the roll may then be packaged and, thereafter, sold or stored for use.

As an additional alternative to any of the above procedures, it is also possible to polymerize the molten polyurethane forming material and then apply it to a bandage or the like. In such a case, it is desirable to use a reaction extruder because the polymerized polyurethane is rather viscous. Also it may be desirable to add a urethane catalyst to speed up the reaction. Typically, the procedure would be to combine the polyol, the polyisocyanate and urethane catalyst in a heated mixer and extruder. The polymerization reaction should take place instantaneously but, notwithstanding, the material is retained in the extruder for a sufficient time to give uniform mixing.

Either before or after the polymerization reaction is completed, the material is extruded onto a suitable bandage substrate to impregnate or coat the substrate. If further polymerization is necessary, the impregnated or coated bandage material may then be heated in an oven or the like in flat or roll form, to advance polymerization to the stage desired. As aforesaid, either before or after the polymer crystallizes, the roll form may be packaged or, if not in roll form, a roll may be formed and then packaged and, thereafter, sold or stored for subsequent use. However, it should be obvious that if the bandage is to be used immediately the steps of forming it into a roll and/or permitting it to crystallize may be dispensed with. It should also be apparent that the polyurethane polymer can be permitted to crystallize and, thereafter, be reheated to a molten state and used as above.

A preferred packaging arrangement includes enclosing or wrapping the impregnated or coated bandage material in polyethylene, such as a polyethylene bag. The packaged material may be kept at room temperature for a long period of time, e.g., from at least one to five years and, under better conditions, up to ten years or more.

Should the polyurethane polymer be NCO (isocyanate) rich, it will react with water in the air or in the fabric while in the oven to form a NCO free product. On the other hand, if the polyurethane polymer is OH (hydroxyl) rich the molecular weight of the polymer will be slightly lowered. In either case, the ratio of the ingredients or the amount of additive used should be such as to produce a product which crystallizes in 2 to 40 minutes when standing at room temperature.

When the bandage is needed, the coated or impregnated bandage is heated in an oven or with any other heat source to melt the polymer at a temperature below 140° F (60° C). When the patient is ready, the bandage is removed from the oven. It may be cooled to room temperature or it may be applied immediately as by unwrapping the bandage from a roll and wrapping it to the afflicted portion of the body. The length of "open time" permits ready manipulation of the surgical or body dressing and facilitates effecting intimate contact between layers or portions of layers of the dressing, such that the overlapping self-adhesive or cohesive polymer material coalesces to ultimately provide a strong cast or body support. Upon standing at room temperature for about 2 to 40 minutes, the polyurethane polymer crystallizes providing a strong, durable, rigid support or cast. The polymer may be slightly cross linked but should be essentially crystalline for best results.

From the foregoing, it will be obvious to those skilled in the art, that pigments, colorants and the like may also be added to the polymeric material used in this invention, if desired. Moreover, it will be apparent that tape, bandage, net materials or the like may be used as a substrate and that thin or multi-layer supportive wrappings may be produced. Those skilled in the art will also recognize the obvious advantages of using a low viscosity, suitable molecular weight resin that will gain viscosity on the bandage; the provision of supportive wrapping material in roll form; the use of polyurethane which is known to be tough and possess good low temperature properties; the ability to unwrap the supportive wrapping by providing slight heat even with a hair dryer; the ability to remove the bandage, reset a bond and reuse the bandage; the desirability of room temperature storage, application and setting of the supportive wrapping; the ability of the bandage to self adhere to obtain strength; the capability of subsequently using material left on a roll, as well as left over polymeric material previously used in making a supportive wrapping; and the absence of water, solvents, monomeric reactions and/or other chemicology.

In addition to that which is specifically disclosed, numerous other techniques of preparation, application and/or use within the purview of this invention will occur to those skilled in the art. For example, the particular means employed for coating, impregnating, casting, spreading or otherwise dispensing the molten polyurethane polymer onto a suitable bandage material according to this invention is intended to encompass all such known means. Moreover, preformed shapes to provide ready made casts, splints or the like are considered to be within the contemplation of this invention. Accordingly, it should be understood that, within the scope of the appended claims, the invention may be practiced otherwise than as specifically described.

We claim:

1. A method of producing a supportive wrapping for a body support comprising,
    impregnating a bandage substrate with a crystallizable polyurethane comprised of the reaction product of a normally crystalline polyol selected from the group consisting of a polyester diol and a polyether diol having a melting point below 121.1° C and a molecular weight greater than 750 and a polyisocyanate present in an amount between 5 and 45 percent by weight based on the total weight of the two constituents,
    said impregnated bandage substrate being impregnated with a molten polyurethane polymer that is crystallizable in a predetermined, delayed time period at temperatures tolerable to human skin,
    heating said bandage material to a temperature above the melting point of said polyurethane polymer and below a temperature intolerable to human skin,
    said bandage substrate impregnated with said crystallized polyurethane having self-adhesive properties at elevated temperatures,
    thereafter wrapping a body member with said heated bandage so that portions of said bandage adhesively adhere to other portions of said bandage and shaping said bandage so that it conforms to the form of the body member, and
    cooling said bandage to room temperature and permitting the polyurethane polymer to crystallize and harden on the bandage material to form the desired rigid supportive wrapping on the body member.

2. A method according to claim 1 wherein the predetermined delayed time period is from 2 to 40 minutes.

3. A method according to claim 1 wherein the temperatures tolerable to human skin are from 6.6° to 65.5° C.

4. A method according to claim 1 wherein a reaction constituent of the polyurethane polymer is polyisocyanate present in an amount sufficient to delay crystallization upon cooling for a predetermined period of time.

5. The method according to claim 1 which includes impregnating said bandage material with a molten polyurethane forming material and, thereafter, polymerizing said forming material to provide said bandage impregnated with said molten polyurethane polymer.

* * * * *